US011737914B2

(12) United States Patent
Taylor et al.

(10) Patent No.: US 11,737,914 B2
(45) Date of Patent: Aug. 29, 2023

(54) THERMAL TREATMENT DEVICES

(71) Applicant: Stryker Corporation, Kalamazoo, MI (US)

(72) Inventors: Gregory S. Taylor, Kalamazoo, MI (US); Alexey Titov, Redmond, WA (US); Hieu Phan, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 1024 days.

(21) Appl. No.: 16/187,755

(22) Filed: Nov. 12, 2018

(65) Prior Publication Data

US 2019/0151141 A1 May 23, 2019

Related U.S. Application Data

(60) Provisional application No. 62/660,560, filed on Apr. 20, 2018, provisional application No. 62/587,902, filed on Nov. 17, 2017.

(51) Int. Cl.
*A61F 7/00* (2006.01)
*A61B 18/02* (2006.01)
*A61B 18/04* (2006.01)
*A61F 7/02* (2006.01)
*A61B 18/00* (2006.01)

(52) U.S. Cl.
CPC ............ *A61F 7/0097* (2013.01); *A61B 18/02* (2013.01); *A61B 18/04* (2013.01); *A61F 7/02* (2013.01); *A61B 2018/00797* (2013.01); *A61B 2018/00863* (2013.01); *A61F 7/0085* (2013.01); *A61F 2007/0054* (2013.01); *A61F 2007/0204* (2013.01); *A61F 2007/0211* (2013.01); *A61F 2007/0239* (2013.01);
(Continued)

(58) Field of Classification Search
CPC ...... A61F 2007/0054; A61F 2007/0204; A61F 2007/0211; A61F 2007/0239; A61F 2007/0246; A61F 2007/0249; A61F 2007/0292; A61F 7/0085; A61F 7/0097; A61F 7/02
See application file for complete search history.

(56) References Cited

U.S. PATENT DOCUMENTS 2,250,325 A  7/1941 Barnes
3,276,935 A  10/1966 Dugan et al.
(Continued)

FOREIGN PATENT DOCUMENTS

CN  208134154  11/2018
GB  2 290 959  1/1996
(Continued)

*Primary Examiner* — Tigist S Demie
(74) *Attorney, Agent, or Firm* — Warner Norcross + Judd LLP

(57) ABSTRACT

A temperature management device for warming or cooling a person's body includes a device body, which has a fluid conduit for flowing fluid through the device body. The device body includes a contact surface to face and contact the person's body on which the device body is applied and is configured to conform to the person's body wherein the contact surface contacts the person's body and follows a surface topography of the person's body, and further provides a thermally conductive surface for transmitting thermal energy from the fluid flowing through the fluid conduit to the person's body.

21 Claims, 7 Drawing Sheets

(52) U.S. Cl.
CPC ............... *A61F 2007/0246* (2013.01); *A61F 2007/0249* (2013.01); *A61F 2007/0292* (2013.01)

(56) References Cited

U.S. PATENT DOCUMENTS

| | | | |
|---|---|---|---|
| 4,154,245 A | 5/1979 | Daily | |
| 4,671,267 A | 6/1987 | Stout | |
| 5,183,039 A | 2/1993 | Sarian et al. | |
| 5,184,112 A | 2/1993 | Gusakov | |
| 5,195,199 A | 3/1993 | Sereboff | |
| 5,336,255 A | 8/1994 | Kanare et al. | |
| 5,391,198 A | 2/1995 | Cheney et al. | |
| 5,456,701 A | 10/1995 | Stout | |
| 5,486,206 A * | 1/1996 | Avery | A61F 7/02 607/104 |
| 5,486,207 A | 1/1996 | Mahawili | |
| 6,113,626 A | 9/2000 | Clifton et al. | |
| 6,141,801 A | 11/2000 | Helenick | |
| 6,197,045 B1 | 3/2001 | Carson | |
| 6,375,633 B1 | 4/2002 | Endress et al. | |
| 6,375,673 B1 | 4/2002 | Clifton et al. | |
| 6,375,674 B1 | 4/2002 | Carson | |
| 6,548,728 B1 | 4/2003 | Faries, Jr. et al. | |
| 6,648,905 B2 | 11/2003 | Hoglund et al. | |
| 6,669,715 B2 | 12/2003 | Hoglund et al. | |
| 6,764,502 B2 | 7/2004 | Bieberich | |
| 6,799,063 B2 | 9/2004 | Carson | |
| 6,927,316 B1 | 8/2005 | Faries, Jr. et al. | |
| 6,962,600 B2 | 11/2005 | Lennox et al. | |
| 7,041,122 B2 | 5/2006 | Paolini et al. | |
| 7,678,716 B2 | 3/2010 | Yahiaoui et al. | |
| 7,744,640 B1 | 6/2010 | Faries, Jr. et al. | |
| 8,021,360 B2 | 9/2011 | Dunning et al. | |
| 8,793,821 B2 | 8/2014 | Fowkes et al. | |
| 9,089,462 B1 | 7/2015 | Lafleche | |
| 9,333,112 B2 | 5/2016 | Carson | |
| 10,555,848 B2 | 2/2020 | Sachdev et al. | |
| 10,835,414 B2 | 11/2020 | Stephan | |
| 2002/0096311 A1 * | 7/2002 | Kushnir | A61F 7/02 165/46 |
| 2007/0073368 A1 | 3/2007 | Cazzini et al. | |
| 2007/0100404 A1 | 5/2007 | Ko et al. | |
| 2009/0112298 A1 | 4/2009 | Jusiak et al. | |
| 2010/0145421 A1 | 6/2010 | Tomlinson et al. | |
| 2011/0066217 A1 * | 3/2011 | Diller | A61F 7/00 607/108 |
| 2018/0042763 A1 | 2/2018 | Galer et al. | |

FOREIGN PATENT DOCUMENTS

| | | |
|---|---|---|
| GB | 2 447 287 | 9/2008 |
| WO | 96/28056 A1 | 9/1996 |

* cited by examiner

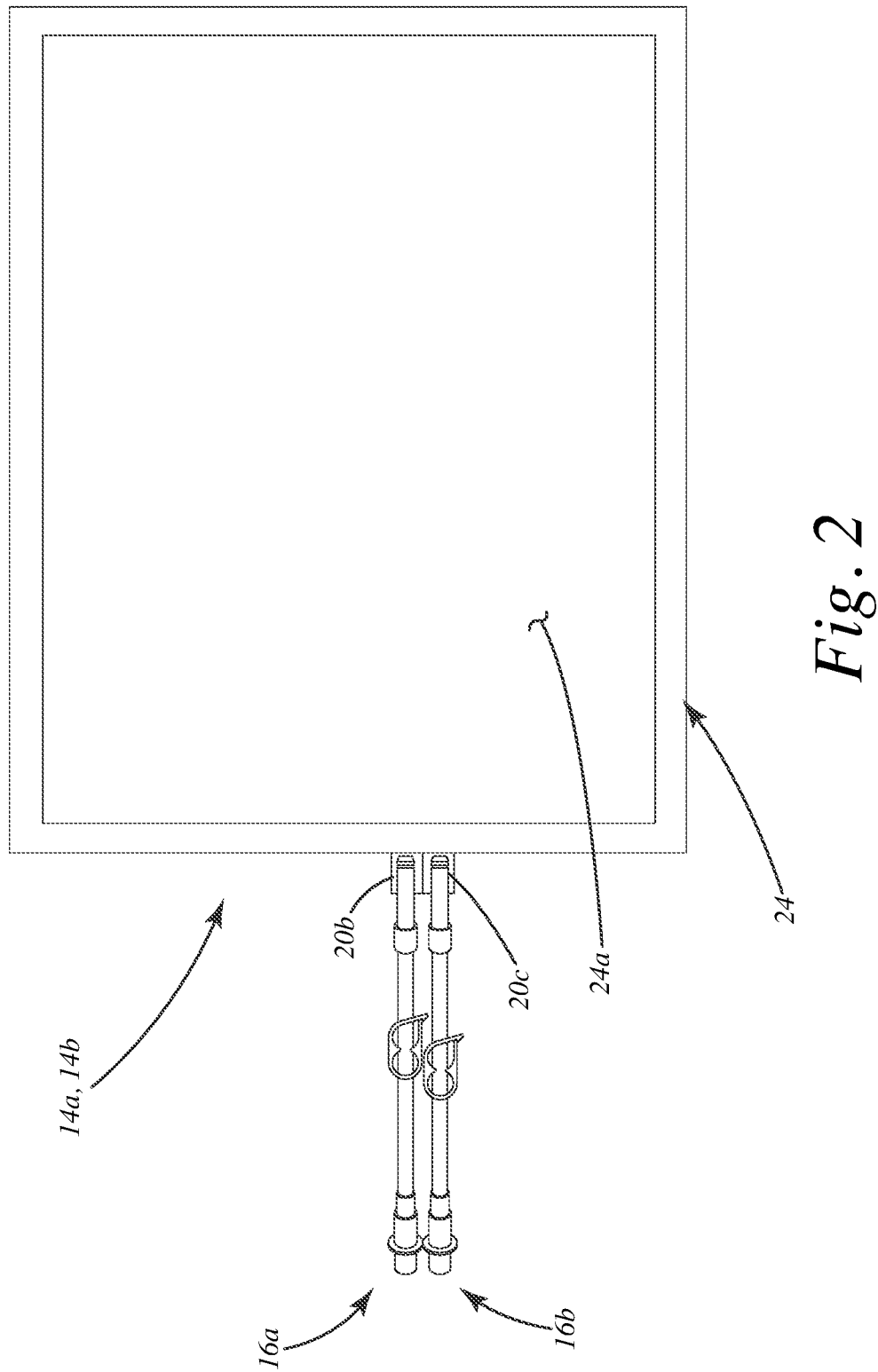

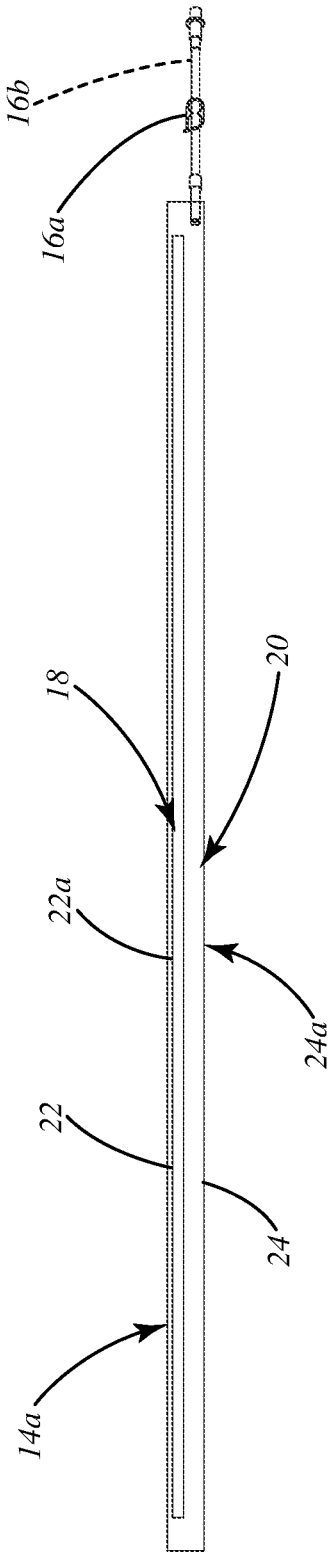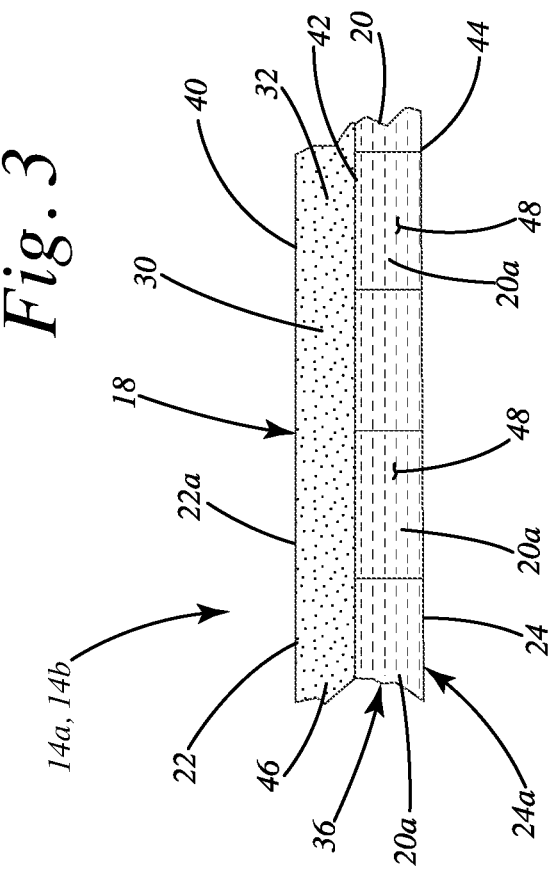

THERMAL TREATMENT DEVICES

This application claims the benefit of U.S. Provisional Application Ser. No. 62/587,902 filed Nov. 17, 2017, entitled THERMAL TREATMENT DEVICES and U.S. Provisional Application Ser. No. 62/660,560 filed Apr. 20, 2018, entitled MAGNETORHEOLOGICAL ELASTOMER AND MAGNETORHEOLOGICAL FLUID FOR CLINICAL WRAP, which are incorporated by reference herein in their entireties.

BACKGROUND

The present disclosure relates to thermal pads or blankets that are placed on or about a patient and which receive temperature controlled fluid in order to control the patient's temperature.

In order to increase the thermal transmission between the pad or blanket and the patient, some pads have an adhesive layer applied to the patient facing side of the pad to maintain contact between the pad and the patient. Other pads or blankets are heavily weighted so that they conform to the patient's body.

There is a need for a thermal pad or blanket that can conform to a patient but without some attendant issues that may be associated with the adhesive layers or added weight.

SUMMARY

The present disclosure provides various improved aspects to thermal pads that are used as part of a thermal control system.

According to one embodiment of the present disclosure, a temperature management device for warming or cooling a person's body includes a device body, which has a fluid conduit for flowing thermal fluid through the device body. The device body includes a contact surface to face and contact the person's body on which the device body is applied. The device body is configured to conform to the person's body wherein the contact surface contacts the person's body and follows a surface topography of the person's body, and further provides a thermally conductive surface for transmitting thermal energy from the fluid flowing through the fluid conduit to the person's body.

In one aspect, the device body includes a granular material to assist the device body to conform to the person's body. Optionally, the granular material comprises a granular material with a density greater than the density of the fluid.

In a further aspect, the granular material comprises a thermally conductive or thermally insulative material (i.e. thermal insulating material). For example, the granular material may comprise a material selected from the group consisting of metal, sand, silica, glass, and ceramic.

In another aspect, the granular material is located in discrete locations in the device body.

In yet other aspects, the granular material forms a continuous layer of granular material. Optionally, the continuous layer of granular material is extended over or along the contact surface to distribute the weight of the granular material over the contact surface and thereby apply a distributed load, and optionally a generally uniformly distributed load, on a person's body.

In one embodiment, the fluid conduit extends through the granular material.

In another embodiment, the granular material is located between the fluid conduit and the contact surface.

According to yet another embodiment, the device body includes an exterior surface facing outwardly from a person when the device body is applied to a person's body, and the granular material is located between the fluid conduit and the exterior surface.

In yet another embodiment, the temperature management device further includes at least one removable insert in the device body, with the removable insert including the granular material.

According to yet another embodiment, a device body holds a layer of thermally conductive material, with the layer of thermally conductive material assisting the device body to conform to the person's body.

In one aspect, the layer of thermally conductive material forms the person contact surface.

In yet another embodiment, the layer of thermally conductive material comprises a layer of memory material or phase transition material. For example, the thermally conductive material may comprise a memory foam or a magnetorheological fluid.

In any of the above temperature management devices, the contact surface is an adhesive free contact surface.

In any of the above temperature management devices, the device body may have an exterior surface and a thickness from the contact surface to the exterior surface in a range of about ¼ to ¾ inches (6 to 19 mm).

In any of the above temperature management devices, the contact surface of the device body may have a contact surface area in a range of 250 to 2,000 square inches (1,613 to 13,000 square cm).

In any of the above temperature management devices, the device body may have a weight in a range of 5 to 12 lbs. (2 to 5.5 kg).

In any of the above temperature management devices, the device body includes one or more enclosed cavities holding a conforming fluid, which assists the device body to conform to the person's body and provides a thermal medium in the device body. Optionally the fluid may comprise a nanofluid or a magnetorheological fluid.

In any of the above temperature management devices, the device further includes a pump coupled to the device body to generate a reduced pressure, such as a vacuum, between the contact surface and a person's body when the device body is applied to the person's body and the pump is operated.

In any of the above temperature management devices, the contact surface is porous.

In any of the above temperature management devices, wherein at least a portion of the temperature management device is disposable.

In yet another embodiment, a temperature management device for warming or cooling a person's body includes a device body, which has a fluid conduit for flowing fluid through the device body. The device body includes a contact surface to face and contact the person's body on which the device body is applied. The device body further includes a weighted layer or region configured to conform the contact surface to the person's body wherein the contact surface contacts the person's body and follows a surface topography of the person's body, and further provides a thermally conductive interface for transmitting thermal energy from the fluid flowing through the fluid conduit to the person's body.

In one aspect, the temperature management device further includes a thermally conductive layer, which forms the contact surface.

In another aspect, the weighted layer or region comprises a layer or region of thermally conductive material selected from the group consisting of metal, sand, silica, and a magnetorheological fluid.

For example, the thermally conductive material may comprise a thermally conductive granular material.

In yet another embodiment, a temperature management device for warming or cooling a person's body includes a fluid passageway for flowing fluid through the temperature management device and a layer of a conformable thermally conductive material, such as a film, to conform the fluid passageway to the person's body to provide heat transfer from the plurality of fluid passageways to the person's body.

In one aspect, the layer includes a plurality of fluid passageways to contact the person's body.

In one embodiment, the layer comprises a spray-on layer, and optionally the layer comprises thermally conductive material.

In one embodiment, the temperature management device further includes a mesh, which forms the plurality of fluid passageways.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 2 is a plan view of a thermal device, in the form of a thermal pad, usable with the thermal control system of the thermal treatment system of FIG. 1;

FIG. 3 is a cross-section of a first embodiment of the thermal device of FIG. 2;

FIG. 3A is an enlarged fragmentary cross-section of the thermal device of FIG. 3;

DETAILED DESCRIPTION OF THE EMBODIMENTS

Figure 1:
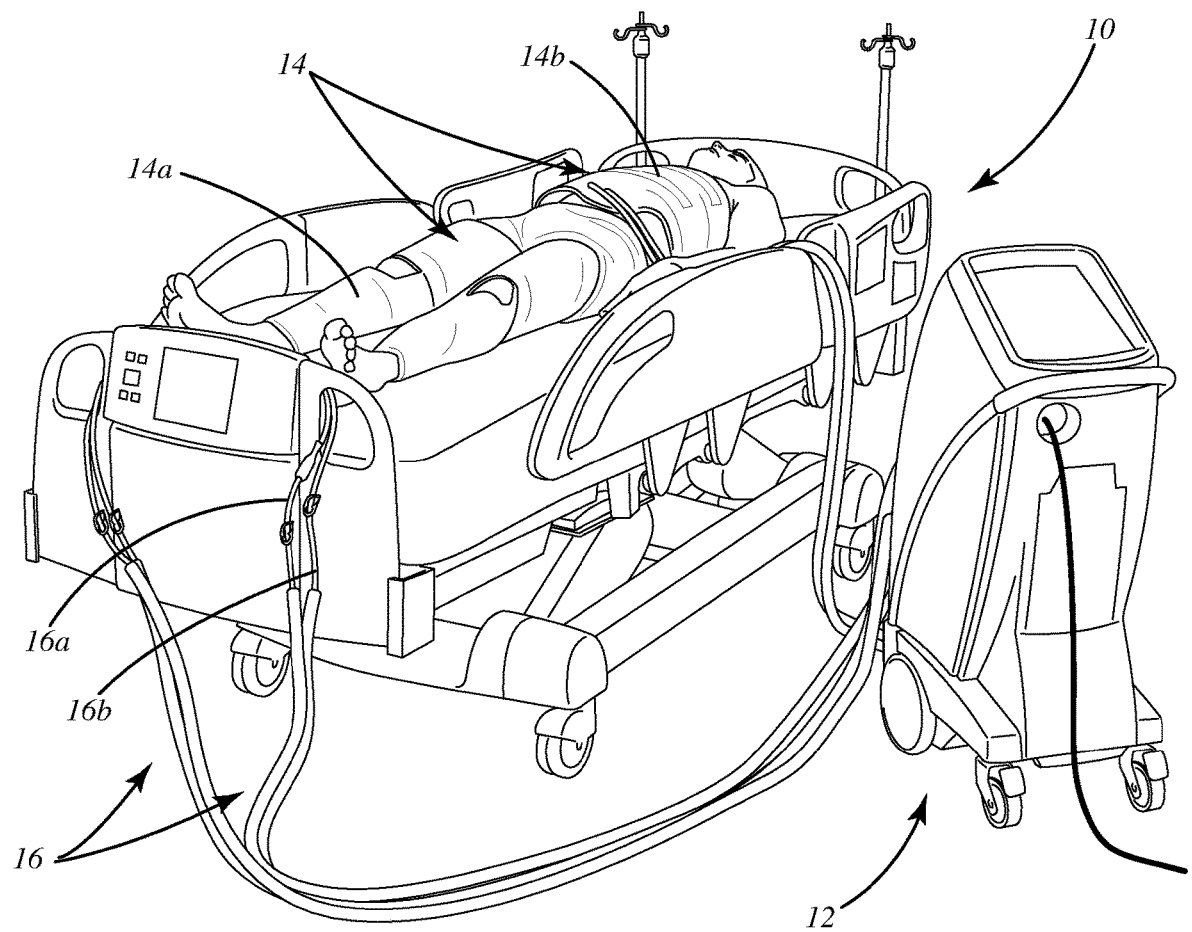
FIG. 1 is a perspective view of an illustrative thermal treatment system that may be used to provide thermal treatment to a patient.

Referring to FIG. 1, the numeral 10 generally designates a thermal treatment system for warming or cooling a patient to thereby control the temperature of a patient, which may involve raising, lowering, or maintaining the patient's temperature, or combinations thereof. Thermal treatment system 10 includes a thermal control unit 12 coupled to one or more thermal treatment devices 14. As will be more fully described below, thermal treatment devices 14 are configured to conform to a person's skin but without the need for adhesive and without the significant weight associated with conventional weighted pads or blankets.

In the illustrated embodiment, thermal treatment devices 14 include a variety of thermal pads (e.g., 14a, 14b, 14', 114, 214, 314, 414) as described below that are each configured to conform to the contours of a portion of a patient's body. For example, the pads may be configured to wrap around a portion of a patient's body, namely a leg or a chest. It should be understood from the forgoing description that the thermal treatment devices 14 may be configured as other types of coverings that can warm or cool a patient, including for example, blankets, vests, patches, leg warmers, caps, or other structure. Although described in the context of several thermal pads, it will be understood by those skilled in the art that this type of device is used for illustrative purposes, and that the term thermal treatment device is to be construed broadly to include all of the different variations of the thermal therapy devices mentioned above (e.g. blankets, vests, patches, leg warmers, caps, etc.). As will be more fully described below, each thermal pad includes a contact surface to face and contact the person's body on which the device body is applied and is configured to conform to the person's body wherein the contact surface contacts the person's body and follows a surface topography or contours of the person's body, and further provides a thermally conductive surface for transmitting thermal energy from fluid flowing through the thermal pad to the person's body.

Referring again to FIG. 1, thermal control unit 12 is coupled to thermal pads 14a, 14b via hoses 16. Each hose 16 may include one or more fluid lines (FIG. 1) with one or more lumens. For example, each hose 16 may include a fluid supply line 16a, a fluid return line 16b, and an auxiliary fluid line (not shown). Thermal control unit 12 delivers temperature controlled fluid (such as, but not limited to, water) to the thermal pads 14a, 14b via supply lines 16a. After the temperature controlled fluid has passed through thermal pads 14a, 14b, thermal control unit 12 receives the temperature controlled fluid back from thermal pads 14a, 14b via a plurality of return lines 16b. The auxiliary lines may be used by thermal control unit 12 in different manners, for example to supply a gas, such as air or oxygen, depending upon the capabilities of thermal control unit 12, the construction of one or more of the thermal pads 14a, 14b, and/or the desired treatment to be applied to the patient. As will be discussed in greater detail below, in some instances thermal control unit 12 may deliver another fluid (as noted above such as a gas, including, air or oxygen) to thermal pads 14a, 14b via the auxiliary line. In other instances, thermal control unit 12 generates negative gauge pressure inside of the auxiliary lines such that fluid inside of one or more chambers (described below) of the thermal pads 14a, 14b, or within the ambient surroundings of the thermal pads 14a, 14b, is drawn back into thermal control unit 12. In still other instances, thermal control unit 12 uses the auxiliary lines to deliver or receive a liquid.

Thermal control unit 12 is adapted to raise or lower the temperature of the fluid supplied to thermal pads 14a, 14b via the supply lines 16a. Thermal control unit 12, therefore, includes a pump and one or more heat exchangers for controlling the temperature of the fluid circulating between thermal control unit 12 and the thermal pads 14a, 14b. Thermal control unit 12 also includes control structures for controlling the pressure of the auxiliary lines (negative or positive) and/or structures for using the auxiliary line to receive or deliver liquid. The construction of thermal control unit 12 may generally take on a variety of different forms to accomplish these tasks. In some embodiments, thermal control unit 12 is constructed in any of the manners disclosed in following commonly assigned patent applications, as modified to enable the thermal control unit 12 to utilize the auxiliary lines to carry out one or more of the functions described in more detail below: U.S. patent application Ser. No. 14/282,383 filed May 20, 2014, by inventors Christopher Hopper et al. and entitled THERMAL CONTROL SYSTEM; U.S. Prov. App. Ser. No. 62/361,124 filed Jul. 12, 2016, by inventor Gregory Taylor and entitled THERMAL CONTROL SYSTEM; and/or U.S. Prov. App. Ser. No. 62/311,054 filed Mar. 21, 2016, by inventor Gregory Taylor and entitled MOBILE THERMAL SYSTEM, which are commonly owned by Stryker Corp. The complete disclosures of all of these applications are hereby incorporated in their entireties by reference herein. The above description also applies to the other embodiments of the thermal pads described herein.

Referring to FIGS. 3 and 3A, each thermal pad 14a, 14b includes a body 18 and a fluid conduit 20 (FIG. 3). Fluid conduit 20 forms a fluid passageway with one or more flow paths 20a (FIG. 3A) for flowing a thermal fluid through body 18. Fluid conduit 20 also includes an inlet 20b and an outlet 20c (FIG. 2) for coupling to the supply lines 16a and return lines 16b of the thermal control unit 12, which supplies and circulates the thermal fluid through the pad, as noted above. Body 18 includes an upper side 22, which forms the exterior surface 22a that faces exteriorly when the pad is applied to a person's body, and a lower side 24, which forms a contact surface 24a to face and contact the person's body on which the body is applied. As will be more fully described in more detail in reference to the various embodiments, body 18 is configured to conform to the person's body so that the contact surface 24a of the lower side 24 contacts the person's body and follows the surface topography of the person's body, and further provides a thermally conductive surface for transmitting thermal energy from the thermal fluid flowing through the fluid conduit 20 to the person's body. Hereinafter reference will be made to pad 14a, but it should be understood the description of pad 14a may apply to pad 14b, as well as the other pads described below, including the pads described in U.S. Pat. Pub. No. US2011/0092890 (P-268A) and U.S. Pat. Nos. 8,048,044 (P-215A) and 8,840,573 (P-394), which are commonly owned by Stryker Corp. and incorporated by reference herein in their entireties.

As best seen in FIG. 3A, body 18 of pad 14a includes a weighted conforming material, such as a granular material 30, to assist the device body 18 to conform to the person's body, while not applying a significant weight to the person's skin or body. For example, in one embodiment, the granular material may comprise a granular material with a density greater than the density of the thermal fluid being directed through body 18. Optionally, the granular material 30 comprises a thermally conductive or thermally, insulative material, to assist in the transfer of heat from the thermal fluid through the pad 14a and the contact surface of the pad 14a. For example, the granular material 30 may comprise a material selected from the group consisting of metal, sand, silica, glass, and ceramic.

In the illustrated embodiment, the granular material 30 forms a continuous layer of granular material 32, and optionally the continuous layer of granular material 32 extends over or at least along the width and/or length of the contact surface 24a formed by lower side 24 of body 18 from one side to the other side of the contact surface and, further, over the body 18 to distribute the weight of the granular material over the contact surface, and thereby apply a distributed load, optionally a generally uniformly distributed load, on a person's body under the contact surface 24a. As noted above, pad 14a does not apply a significant weight to the person's skin or body, and instead only applies a total weight or load in a range of 7 to 30 lbs. (2 to 13.6 kgs.). Stated another way, pressure exerted by pad 14a may be in a range of 0.1 to 0.2 psi.

In the illustrated embodiment, such as shown in FIG. 3A, the fluid paths 20a are located between the granular material 30 and the contact surface 24a. Further, the fluid paths 20a are arranged so that they are immediately adjacent each other to provide in effect a thermal fluid layer 36 immediately adjacent the contact surface 24a of lower side 24 of the pad. As such, the distributed weight of granular material 30 gently presses the fluid layer 36 and contact surface 24a against the person's body. Thus, in this embodiment, the granular material 30 is located between the fluid conduit 20 and the exterior surface 22a. Accordingly, granular material 30 may comprise an insulative material to insulate fluid conduit 20.

In one embodiment, the fluid conduit 20 is formed by one or more tubes inserted into the cavity that forms the thermal fluid layer. Alternately, as noted, fluid paths 20a may be formed by one or more conduits or passageways formed in the body, for example, when the body is formed from a solid material, or when the body is formed from two or more sheets joined and sealed together, as described below.

Figure 3B:
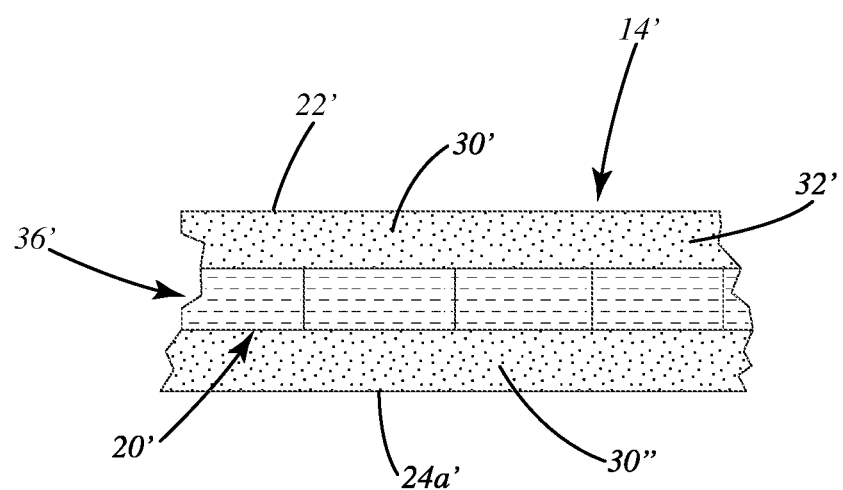
FIG. 3B is an enlarged fragmentary cross-section of a second embodiment of a thermal device.
Figure 4:
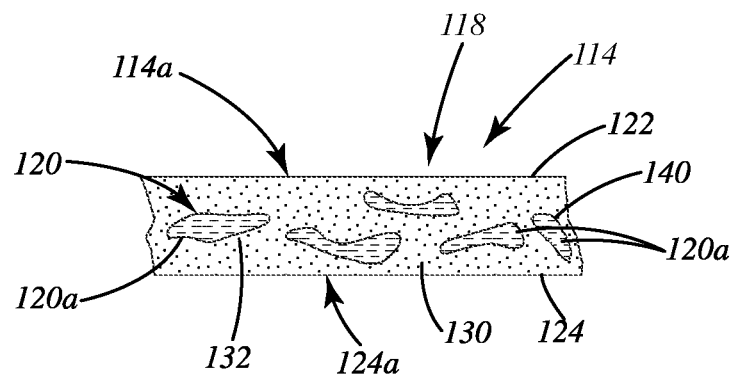
FIG. 4 is an enlarged fragmentary cross-section of a third embodiment of a thermal device.
Figure 5:
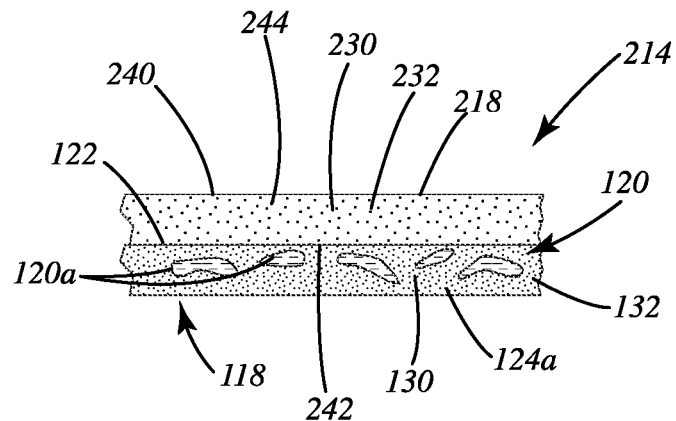
FIG. 5 is an enlarged fragmentary cross-section of a fourth embodiment of a thermal device.
Figure 6:
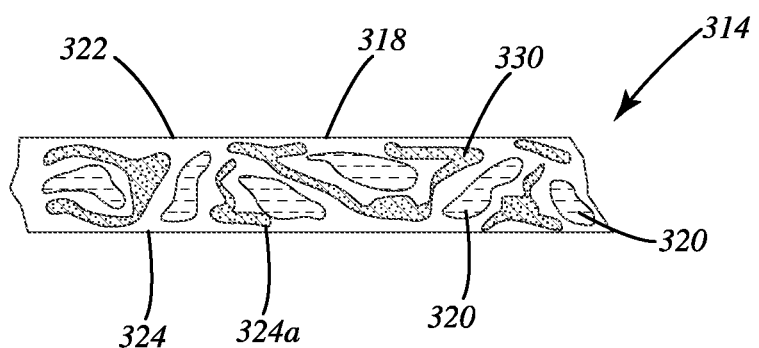
FIG. 6 is an enlarged fragmentary cross-section of a fifth embodiment of a thermal device.

For example, the fluid conduit 20 may be configured in a serpentine arrangement with multiple, generally parallel immediately adjacent fluid paths 20a (such as shown in FIG. 3A) that extend across the width (or length) of the pad or with multiple, generally parallel spaced apart fluid paths, such as shown and described in reference to the embodiments illustrated in FIGS. 4-6. Alternately, two or more separate or independent conduits may be provided to provide independent fluid paths through the pad.

Similarly the granular material, as noted, may extend generally along the full width and/or length of the pad or may be segregated into discrete regions across the pad.

For example, body 18 may be formed from one, two, or three sheets of flexible, conformable material, such as a polyester and/or nylon or a composite thereof, joined together, such as by heat sealing, welding, or an adhesive to form the perimeter of the pad and two or more cavities therein for forming or holding the fluid conduit 20 and/or for holding the granular material 30. Welding may include heat welding, ultrasonic welding, Radio Frequency (RF) welding, or by other types of welding.

In the illustrated embodiment, body 18 is formed from three spaced sheets 40, 42, and 44 (FIG. 3A), which are bonded or welded at their perimeters to form pad 14a. The space interior between the sheets 40 and 42 where they are not welded or bonded to each other (namely interior of the perimeter of the pad) defines a first chamber 46 for holding the granular material 30. Sheets 42 and 44 are additionally joined at spaced intervals interior of the perimeter. The spaces interior between the sheets 42 and 44 where they are not welded or bonded to each other define a plurality of chambers 48, which share a weld or bond with their adjacent chambers for forming the fluid paths. Optionally, interior walls may be provided between sheets 42 and 44 so that chambers 48 are separated by walls and not just welds or bonding.

Further, the bonds or welds (or walls) between sheets 42 and 44 maybe joined together internally of the perimeter by a plurality of spaced welds that are shorter than the length or width of the cavity (or pad) and are staggered to form a serpentine fluid path that allows all the fluid flow paths to communicate with each adjacent fluid path at alternating ends. Alternately, the welds may be aligned but terminate at the same distance from the perimeter either at both ends, or on one end, so that the spaces between their terminal ends and the perimeter form, passages or a transverse passage, that allow all the fluid flow paths to communicate with each other through the transverse passages or passage. For examples of optional fluid paths that may be formed in pad 14a, reference is made to U.S. Pat. Nos. 5,184,112; 5,183,039; 6,113,626; 6,375,633; 6,375,673; 7,041,122; and 9,089,462, and U.S. Pat. Pub. Nos. 2007/0073368 and 2009/0112298, which are commonly owned by Stryker Corporation and are incorporated by reference herein in their entireties.

Alternately, body 18 may be formed from a solid flexible, conformable material, such as foam or gel, with cavities formed therein to form the fluid conduit (or to receive tubes inserted into the solid flexible conformal material to form the fluid conduit) and one or more cavities to hold the granular material.

Referring again to FIG. 3A, as noted above, the thermal fluid layer may be between the granular layer 32 and the contact surface 24a. As will be more fully described below, a second granular layer may be provided and/or the granular material 30 may be located in discrete locations in the device body. Further, pad 14a may include a removable insert in the device body 18 with the removable insert including granular material 30.

Additionally, where two or more granular materials are used, the granular materials may be different and have different properties and/or characteristics. For example, the granular materials may be the same or may vary and have different substrate size and/or have different thermal properties—for example, one or more of the granular materials may be thermally insulative or one or more of the granular materials may have thermal transmission properties. Further as noted above, the granular materials may each form a continuous layer or may be provided in discrete regions or a combination of both.

Referring to FIG. 3B, pad 14', which is of similar construction to pad 14a, includes a second conforming material, such as a granular material 30", which is located between thermal fluid conduit 20' and contact surface 24a' of pad 14'. Similar to pad 14a, pad 14' includes a first granular material 30', which forms a first granular material layer 32' between exterior facing side 22' of pad 14' and thermal fluid conduit 20' (and hence thermal fluid layer 36'). In this manner, granular material 30" may be a thermally conductive, conforming material to provide heat transmission between the fluid flowing through conduit 20' and the contact surface 24a' of pad 14' and, further, between pad 14' and person wearing the pad 14'.

Granular material 30', on the other hand, thus need not be a thermally conductive material and instead may be an insulation material, as well as a conforming material to assist in conforming the pad 14' to the person wearing the pad. Thus, the granular materials (30' and 30") may be different. However it should be understood that the granular materials (30' and 30") may also be the same. For details of the construction of pad 14' and conduit 20' not expressly stated herein reference is made to pad 14a.

Referring to FIG. 4, the numeral 114 designate another embodiment of a pad. As noted above, the term pad is used for ease of illustration of the present disclosure is not limited to a pad. Similar to pad 14a, pad 114 includes body 118 with a granular material 130 and a fluid conduit 120. In the illustrated embodiment, fluid conduit 120 is located in the granular material 130, which similarly extends along or across pad 114 and forms a generally continuous granular layer 132. For example, conduit 120 may be formed from tubing 140 that extends through the granular material 130 and which includes an inlet and an outlet for coupling to the supply line (16a) and return line (16b) of the thermal control unit 12, which supplies and circulates the thermal fluid through the pad, as noted above.

In one embodiment, tubing 140 may have a serpentine configuration to form spaced apart fluid paths 120a, including generally parallel spaced apart fluid paths. In another embodiment, tubing 140 may form two independent conduits, each conduit with its own inlet and own outlet to thereby form an independent fluid path.

Optionally, tubing 140 may be located at or adjacent contact surface 124a of pad 114 or may be spaced from contact surface 124a. When spaced from contact surface 124a, granular material 130, as noted above, may comprise a thermally conductive material to provide heat transfer from the thermal fluid flowing through tubing 140.

In one embodiment, body 118 of pad 114 is formed from two or more sheets of flexible conformable material, which are welded together in a similar manner as described above.

Alternately, body 118 may be formed from a solid body of material, such as foam or gel, with the granular material embedded in the gel or foam in a cavity or cavities formed therein, such as described above, or distributed or disperse through a portion of the solid body or throughout the solid body.

Tubing 140 may then be embedded in the granular material 130. For example, tubing 140 may be inserted in the granular material during the forming process. When formed from a solid material, tubing 140 may be inserted into the granular material or sold material during molding. When body 118 of pad 114 is formed from two or more sheets of flexible material, tubing 140 may be placed between the two or more sheets before the sheets are joined together, such as by welding.

Tubing 140 may be located throughout the granular material as shown, or may be located closer to the contact surface 124a. In this manner, at least some of the granular material, is located between the fluid conduit 120 and the contact surface 124a and, therefore, as noted may comprise a thermally conductive granular material to provide heat transfer from the thermal fluid flowing through tubing 140 to the contact surface 124a and to the person underlying the contact surface 124a.

Referring to FIG. 5, the numeral 214 designates another embodiment of a pad. Pad 214 may be formed from a second body 218 as well as body 118 of pad 114, or a similar pad, including pad 14a, but includes the addition of a second granular material 230, which forms a second granular layer 232. For example, second granular material 230 may be enclosed in a cavity 244 formed between upper and lower sheets 240, 242 of flexible material, which are joined along their perimeters, for example by an adhesive or welding, which in turn is then joined with pad 114, for example by an adhesive or by welding. Alternately, second granular material 230 may be enclosed by a cavity formed by sheet 240 joined with pad 114 on its upper side 122, for example, by welding or an adhesive, so that the second granular material is captured between the sheet 240 and the sheet that forms the upper side 122 of pad 114.

Alternately, granular material 230 may be formed in or integrated into a solid body as described above. Therefore, in one embodiment, body 218 of pad 214 may comprise a solid, but flexible conformable material pad, for example, formed from gel or foam, which is then joined with pad 114, such as by the adhesive or welding.

In another embodiment, pad 214 may be formed from two discrete pads each formed, such as by molding, from a solid, but flexible conformable material with cavities formed therein to hold the two granular materials and the conduit, such as described above.

For example, the granular material 130 in pad 114 may be a conductive granular material, while granular material 230 may be a less conductive material and provide an insulation function rather than a heat transmission function. Though it should be understood that both granular materials 130, 230 may provide a heat transmission function, in addition to the weighted conforming function describe above.

In this manner, tubing 140 and granular material 130 are located between granular material 230 and contact surface 124a of pad 114.

Referring to FIG. 6, the numeral 314 designates yet another embodiment of a temperature treatment pad. Pad 314 also includes a body 318 with a weighted conforming material 330 and a thermal fluid conduit 320 therein, which passes through material 330 similar to pad 114. In the illustrated embodiment, weighted conforming material 330 comprises a smart material that changes shape in response to an external stimulus, such as heat or electricity. For example, a suitable smart material changes its elasticity in response to stimuli.

In one embodiment, weighted conforming material 330 comprises a layer of memory material or a material that exhibits a property change based on an input, such as a material undergoing state or phase transition during thermal treatment process, such as when heating or cooling is applied, for example, as the cool or warm fluid is flowed through the pad or otherwise applied. For example, the weighted conforming material 330 may comprise a memory foam or paraffin, or a magnetorheological fluid, such as an MR fluid or a nanofluid, which has a carrier fluid and magnetic particles (such as iron particles) suspended in the fluid, and which changes its viscosity when a magnetic field is applied. When using a shape retaining material, such as a "memory foam" or paraffin, the pad is pressed onto the person's body and under the pressure will conform to the person's body. When using an MR fluid, a magnetic field is applied, and the MR fluid or nanofluid will have a greater viscosity so that it acts more like viscoelastic material—and, as a result, is non-conforming. The pad can then be applied to the person's body and the magnetic field is removed so that the MR fluid will become less viscous and flow so that it conforms to the person's body, before resuming the application of the magnetic field. For example, the magnetic field may be produced by a circuit, a coil, or one or more magnets, including one or more electromagnets and a corresponding electromagnet control circuit, all of which may be incorporated into the pad or device used with the pad.

In one embodiment, material 330 is state transition material that is elastic and conformable until an electrical current or heat is applied to the material. To apply an electrical current (or voltage) to material 330, electrically conductive contacts 330a, 330b (FIG. 7) are embedded in the material 330. Electrically conductive contacts 330a, 330b are then coupled to an electrical or voltage load via electrical conductors, such as wires, that couple to a voltage supply, such as a battery. For example, the current or voltage may be supplied by on-board voltage supply and, further, controlled by a controller. The controller and/or voltage supply may be mounted to the pad or may be provided by thermal control unit 12.

Figure 7:
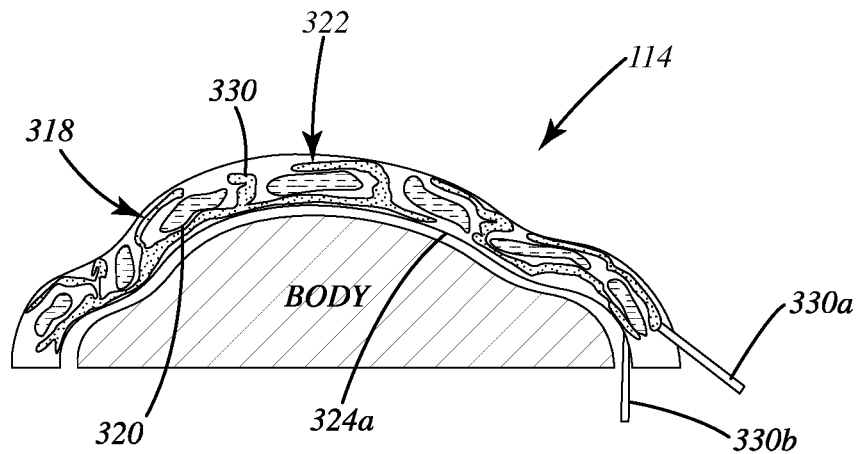
FIG. 7 is a cross-section of the thermal device of FIG. 6 and shown applied to and following the surface topography of a person's body.

In use, as shown in FIG. 7, before electricity or voltage is applied to the contacts 330a, 330b, pad 314 is placed about a person's body where treatment is to be applied. Until the electrical current or heat is applied to material 330, material 330 will conform under its own weight to the surface topology of a person's body. Once the pad 314 is in position and is conformed to the person body, electrical current or voltage can then be applied to material 330 so that material 330 will set its shape and maintain contact with a person's body, while still following the contours of the person's body, even after the thermal fluid flows through passageway through the conduit 320. In this manner, the pressure of the fluid in conduit 320 will not cause the pad to change its shape or apply more pressure to the person's skin.

Figure 8:
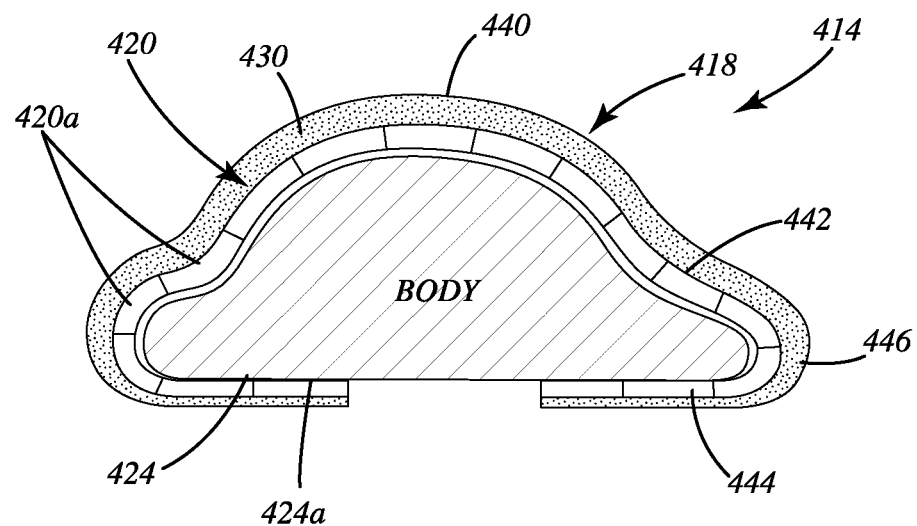
FIG. 8 is an enlarged fragmentary cross-section of a sixth embodiment of a thermal device.

Instead of, or in addition to, the granular or solid conforming material, any of the conforming pads may incorporate a fluid to assist in conforming the pad to the contours of a person's body. For example, referring to FIG. 8, pad 414 includes a fluid conforming layer 430 and fluid conduit 420 (similar to the previous embodiments) that forms a plurality of fluid paths 420a that extend through pad 414. Body 418 of pad 414 may be constructed, as described above, from a solid, but flexible, conforming material or from sheets of flexible 440, 442, 444 and conforming material, which form or have cavities formed therein for holding the conforming layer and for holding tubing to form the conduit (or the conduit may be formed by the material forming the pad).

In one embodiment, the fluid in fluid conforming layer 430 is a fluid, such as air or nanofluid, which is pressurized or depressurized to conform the pad to the contours of the person's body. For example, as noted above, thermal control unit 12 may supply the fluid or may suction the fluid from pad 414 to cause pad 414 to conform to the person's body, such as shown in FIG. 7. When used to apply suction to the patient, thermal control unit 12 generates a negative gauge pressure inside of chamber 446 that is large enough to create a suction force between thermal pad 414 and the patient's skin, thereby helping to ensure that contact surface 424a of lower side 424 thermal pad 414 stays in, or is drawn into, close contact with the patient's skin. This close contact helps improve the efficiency of the thermal transfer between the patient and thermal pad 414.

In any of the above, the pads may include at least one removable insert in the pad body, with the removable insert including the granular material.

In any of the above temperature management devices, the device body has a thickness from the contact surface to the exterior surface in a range of about ¼ to ¾ inches (6 to 9 mm).

In any of the above temperature management devices, the contact surface of the device body has a contact surface area in a range of 250 to 2,000 square inches (1,613 to 13,000 square cm).

In any of the above temperature management devices, the device body may have a weight in a range of 5 to 12 lbs. (2 to 5.5 kg).

Further, as noted, in any of the above temperature management devices, the contact surface may be an adhesive free contact surface.

In any of the above temperature management devices, the contact surface may be porous. Further, the pad may further include a pump coupled to the pad to generate a reduced pressure as noted, such as a vacuum, between the contact surface and a person's body. The reduced pressure may be applied through the porous contact surface, when the pad is applied to the person's body and the pump is operated. The pump may be provided by the thermal control unit 12 or a separate pump, including a pump mounted to the pad.

In any of the above temperature management devices, at least a portion of the temperature management device is disposable. For example, the pad body and/or the granular material inserts may be disposable.

Thus, a temperature management device for warming or cooling a person's body is disclosed that includes a device body, which has a fluid conduit for flowing fluid through the device body. The device body includes a contact surface to face and contact the person's body on which the device body is applied. The device body further includes a weighted layer or a region configured to conform to the contact surface to the person's body wherein the contact surface contacts the person's body and follows a surface topography of the person's body, and further provides a thermally conductive interface for transmitting thermal energy from the fluid flowing through the fluid conduit to the person's body. In the case where the device body is weighted, the weighted material may be above the fluid (between the fluid conduit and outwardly facing side of the device body), and optionally may be insulative, or it may be beneath the fluid conduit (between the fluid conduit and patient facing side), and optionally may be thermally conductive. Alternately, as described above the weighted material may surround the fluid conduit so that together the weighted material and fluid conduit form a combined, single layer.

Further, the pad may have one or more weighted layers or regions, as noted above, below or surrounding the fluid conduit. When multiple weight layers or regions are used, they may have the same or different weighted, e.g. granular, materials.

In another embodiment, the layer that conforms the thermal fluid layer to contact the person's body may comprise a thin sheet of formable material, such as metal, or a thin sheet of conformable material, such as a flexible film. For example, a spray-on layer may provide the flexible film. Further, the conduit may be formed from a mesh, which forms at least one or a plurality of fluid paths, with the spay-on layer optionally applied after the mesh is applied to the skin.

Figure 9:
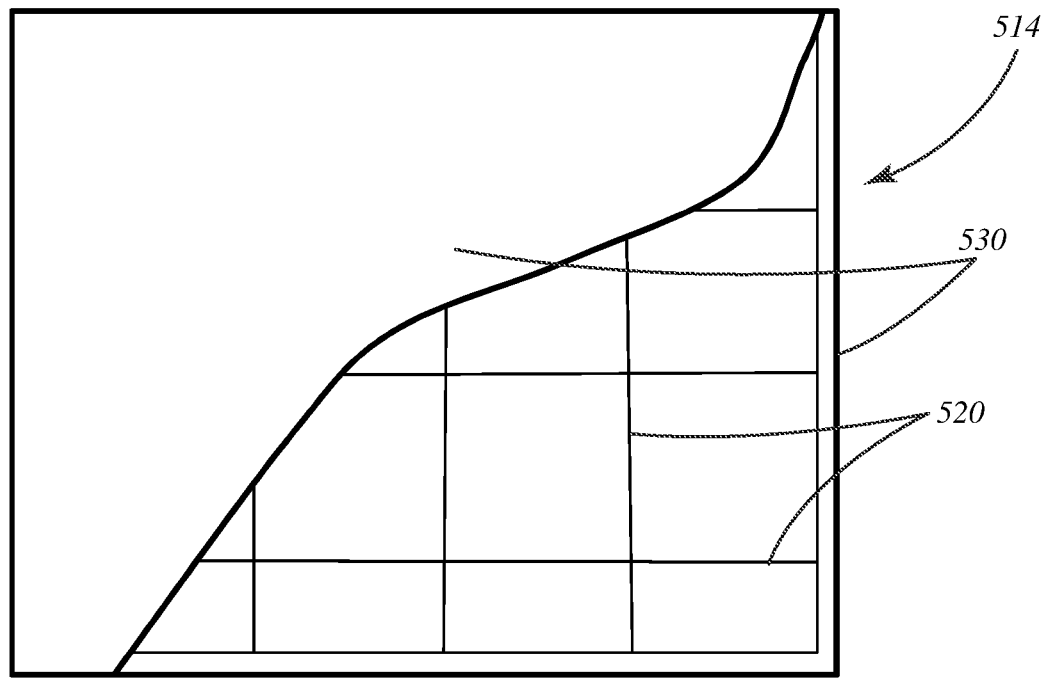
FIG. 9 is a fragmentary plan view of a seventh embodiment of a thermal device.
Figure 10:
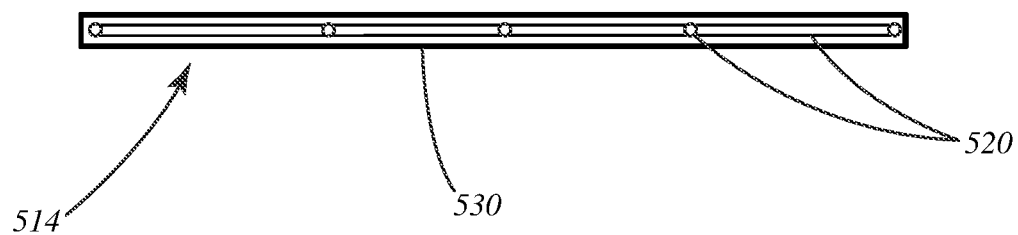
FIG. 10 is a cross-section view of the thermal device of FIG. 9.

Referring to FIGS. 9 and 10, thermal device 514 includes a fluid conduit 520 and layer 530 that conforms the conduit 520 to the person's body and contacts the person's body. Layer 530 comprises a thin sheet of formable material, such as a flexible film. For example, layer 530 may be a spray-on layer. In the illustrated embodiment, the conduit 520 is formed from a mesh of tubes that are in fluid communication with each other to allow fluid flow through the mesh. For example, the mesh may be a serpentine-shaped mesh or a grid like mesh, which forms one or more fluid paths. For example, the spay-on layer may be optionally applied after the mesh is applied to the skin.

Optionally, any of the above pads, may include one or more straps that are used to secure the thermal pad to a patient when in use. Although thermal pad 14a of FIG. 2 is shown as having a generally rectangular shape, it will be understood by those skilled in the art that this may be varied greatly. That is, the thermal pads 14a, 14b may take on any shape that is conducive to being wrapped around one or more portions of a person's body. In some embodiments, those thermal pads 14a, 14b that are intended to be wrapped around the patient's torso have a different shape than those intended to be wrapped around the patient's legs. Those adapted to be wrapped around the patient's legs may include one or more cutouts or contours that allow the patient to bend his or her knees while the thermal pads 14a, 14b are wrapped around his or her legs.

In some embodiments, the thermal pads described herein may be used to apply intermittent pneumatic compression. For example of a suitable thermal control system reference is made to U.S. patent application Ser. No. 15/675,061, filed Aug. 11, 2017 (P-535A) and U.S. Pat. No. 7,972,287, which are commonly owned by Stryker and are incorporated by reference herein in their entireties.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

We claim:

1. A temperature management device for warming or cooling a person's body, said temperature management device comprising:

a device body, said device body having a fluid conduit for flowing a thermal fluid through said device body;

said device body including a contact surface to face and apply a weighted conforming contact to the person's body on which said device body is applied; and said device body having a cavity holding a conformable fill of a plurality of particles collectively forming a granular material wherein the granular material provides the weighted conforming contact to the person's body wherein said contact surface contacts the person's body and follows a surface topography of the person's body and further provides a thermally conductive surface for transmitting thermal energy from the thermal fluid flowing through said fluid conduit to the person's body, wherein the granular material held in the cavity is not embedded in a gel.

2. The temperature management device according to claim 1, wherein said conformable fill has a density greater than the density of the fluid.

3. The temperature management device according to claim 2, wherein said conformable fill comprises a thermally conductive or thermally insulative granular material.

4. The temperature management device according to claim 3, wherein said conformable fill comprises granular material selected from the group consisting of metal, sand, silica, glass, and ceramic.

5. The temperature management device according to claim 2, wherein said conformable fill is located in discrete locations in said device body.

6. The temperature management device according to claim 2, wherein said conformable fill forms a layer of granular material, said layer of granular material extending along said contact surface to apply a distributed load on the person's body under said contact surface.

7. The temperature management device according to claim 2, wherein said fluid conduit extends through said granular material.

8. The temperature management device according to claim 2, wherein said conformable fill is located between said fluid conduit and said contact surface.

9. The temperature management device according to claim 2, wherein said device body includes an exterior surface facing outwardly from the person when said device body is applied to the person's body, and said conformable fill being located between said fluid conduit and said exterior surface.

10. The temperature management device according to claim 2, further comprising at least one removable insert in said device body, said removable insert including said conformable fill.

11. The temperature management device according to claim 2, wherein said granular material comprises a first granular material, said device body further includes a second granular material different than said first granular material.

12. The temperature management device according to claim 1, wherein said contact surface is an adhesive free contact surface.

13. The temperature management device according to claim 1, wherein said device body comprises a pad.

14. The temperature management device according to claim 1, wherein said device body comprises two pads.

15. The temperature management device according to claim 1, wherein said device body includes one or more enclosed cavities holding a conforming fluid, said conforming fluid to assist said device body to conform to the person's body and provide a thermal medium in said device body, and said conforming fluid comprising a nanofluid.

16. The temperature management device according to claim 1, further comprising a pump coupled to said device body to generate a reduced pressure between the contact surface and the person's body when said device body is applied to the person's body and said pump is operated.

17. The temperature management device according to claim 1, wherein said contact surface is porous.

18. The temperature management device according to claim 1, wherein at least a portion of said temperature management device is disposable.

19. A temperature management device for warming or cooling a person's body, said temperature management device comprising:
a device body, said device body having a fluid conduit for flowing fluid through said device body;
said device body including a contact surface to face and contact the person's body on which said device body is applied; and
said device body further including a cavity filled with a conformable fill of granular material arranged in a layer or a region, said fill configured to conform said contact surface to the person's body wherein said contact surface contacts the person's body and follows a surface topography of the person's body and further provides a thermally conductive interface for transmitting thermal energy from the fluid flowing through said fluid conduit to the person's body wherein the granular material provided in the cavity is not embedded in a gel.

20. The temperature management device according to claim 19, further comprising a thermally conductive layer, said thermally conductive layer forming said contact surface.

21. The temperature management device according to claim 19, wherein said layer or region comprises a layer or region of thermally conductive granular material.

* * * * *

UNITED STATES PATENT AND TRADEMARK OFFICE
CERTIFICATE OF CORRECTION

| | |
|---|---|
| PATENT NO. | : 11,737,914 B2 |
| APPLICATION NO. | : 16/187755 |
| DATED | : August 29, 2023 |
| INVENTOR(S) | : Gregory S. Taylor et al. |

It is certified that error appears in the above-identified patent and that said Letters Patent is hereby corrected as shown below:

In the Claims

Column 14, Claim 19, Line 36:
"fluid conduit to the person's body wherein the granular"

Should be:
-- fluid conduit to the person's body, wherein the granular --

Signed and Sealed this
Twenty-sixth Day of March, 2024

Katherine Kelly Vidal
*Director of the United States Patent and Trademark Office*